(12) United States Patent
Pretz

(10) Patent No.: US 9,707,533 B2
(45) Date of Patent: Jul. 18, 2017

(54) FLUIDIZED CATALYST STRIPPING UNIT FOR DISPLACING ENTRAINED GAS FROM CATALYST PARTICLES

(71) Applicant: Dow Global Technologies LLC, Midland, MI (US)

(72) Inventor: Matthew T. Pretz, Lake Jackson, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 14/955,344

(22) Filed: Dec. 1, 2015

(65) Prior Publication Data

US 2017/0151544 A1 Jun. 1, 2017

(51) Int. Cl.
*B01J 8/34* (2006.01)

(52) U.S. Cl.
CPC ........ *B01J 8/34* (2013.01); *B01J 2208/00991* (2013.01)

(58) Field of Classification Search
CPC ............. B01J 8/34; B01J 8/0055; B01J 8/008
See application file for complete search history.

(56) References Cited

U.S. PATENT DOCUMENTS

| | | |
|---|---|---|
| 2,472,502 A | 6/1949 | Tyson |
| 2,481,439 A | 9/1949 | Ogorzaly |
| 2,545,165 A | 3/1951 | Ogorzaly |
| 4,246,231 A | 1/1981 | Figler et al. |
| 4,579,716 A | 4/1986 | Krambeck et al. |
| 4,615,992 A | 10/1986 | Murphy |
| 4,654,060 A | 3/1987 | Haddad et al. |
| 5,190,650 A | 3/1993 | Tammera et al. |
| 5,275,641 A | 1/1994 | Tammera et al. |

(Continued)

FOREIGN PATENT DOCUMENTS

| | | |
|---|---|---|
| WO | WO2007/094771 | 8/2007 |
| WO | 2015073152 A1 | 5/2015 |

OTHER PUBLICATIONS

International Search Report and Written Opinion issued in International Patent Application No. PCT/US2016/064260, dated Feb. 20, 2017, 11 pages.

*Primary Examiner* — Lessanework Seifu
(74) *Attorney, Agent, or Firm* — Dinsmore & Shohl LLP

(57) ABSTRACT

A fluidized catalyst stripping unit for displacing entrained gas from catalyst particles comprising: a vessel housing a two stage cyclonic separation section which comprises one or more primary cyclonic separation devices and one or more secondary cyclones; a stripping section which comprises internals; and an inlet in fluid communication with a catalytic reactor to feed a particulate-fluid suspension to the two stage cyclonic separation section; wherein each primary cyclonic separation device comprises an internal cylindrical surface to separate a major fraction of the particulates from the suspension and form a vortex of reduced particulate content; a particulate discharge outlet from each secondary cyclone to the stripping section; wherein the particulate discharge outlet of the secondary cyclone is submerged in a catalyst bed located above the stripper internals, and wherein the stripping section comprises one or more bubble breaking grids within the catalyst bed and above the stripping internals is provided.

3 Claims, 4 Drawing Sheets

(56) References Cited

U.S. PATENT DOCUMENTS

| | | |
|---|---|---|
| 5,411,710 A | 5/1995 | Iwasyk |
| 5,910,240 A | 6/1999 | Senior et al. |
| 6,680,030 B2 | 1/2004 | Koebel et al. |
| 7,022,221 B1 | 4/2006 | Hedrick |
| 7,077,997 B1 | 7/2006 | Sandacz et al. |
| 7,247,233 B1 * | 7/2007 | Hedrick ................ B01J 8/0055 208/113 |
| 8,669,406 B2 | 3/2014 | Pretz et al. |
| 9,446,398 B2 * | 9/2016 | Palmas .................... B01J 8/26 |
| 2013/0252799 A1 | 9/2013 | Johnson, II et al. |
| 2014/0294685 A1 | 10/2014 | Johnson, II et al. |
| 2014/0296603 A1 | 10/2014 | Johnson, II et al. |

* cited by examiner

FLUIDIZED CATALYST STRIPPING UNIT FOR DISPLACING ENTRAINED GAS FROM CATALYST PARTICLES

FIELD OF INVENTION

The disclosure relates to a fluidized catalyst stripping unit for displacing entrained gas from catalyst particles.

BACKGROUND OF THE INVENTION

In catalytic alkane or alkyl aromatic dehydrogenation processes, reactor secondary cyclone dipleg bypassing and stripper bypassing may occur. In the secondary cyclones, this is believed to occur due to the low solids loading and low dipleg pressure drop which allows gas to flow up the dipleg and cause the secondary cyclone to not be effective at removing particles. Another potential operational problem is that gas bypassing can occur in a fluidized bed of catalyst due to bubble formation in unconstrained fluidized beds operating at low pressure which causes inefficient catalyst stripping. This poor catalyst stripping results in valuable product being transported to the combustor and combusted.

SUMMARY OF THE INVENTION

In one embodiment, the disclosure provides a fluidized catalyst stripping unit for displacing entrained gas from catalyst particles comprising: a vessel which houses a two stage cyclonic separation section which comprises one or more primary cyclonic separation devices and one or more secondary cyclones; a stripping section which comprises internals; and an inlet in fluid communication with a catalytic reactor to feed a particulate-fluid suspension to the two stage cyclonic separation section; wherein each primary cyclonic separation device comprises an internal cylindrical surface to separate a major fraction of the particulates from the suspension and form a vortex of reduced particulate content; a particulate discharge outlet from each secondary cyclone to the stripping section; wherein the particulate discharge outlet of the secondary cyclone is submerged in a catalyst bed which is located above the stripper internals within the stripping section, and wherein the stripping section comprises one or more first bubble breaking grids located above the stripping section internals and below the catalyst level.

DETAILED DESCRIPTION OF THE INVENTION

Figure 1:
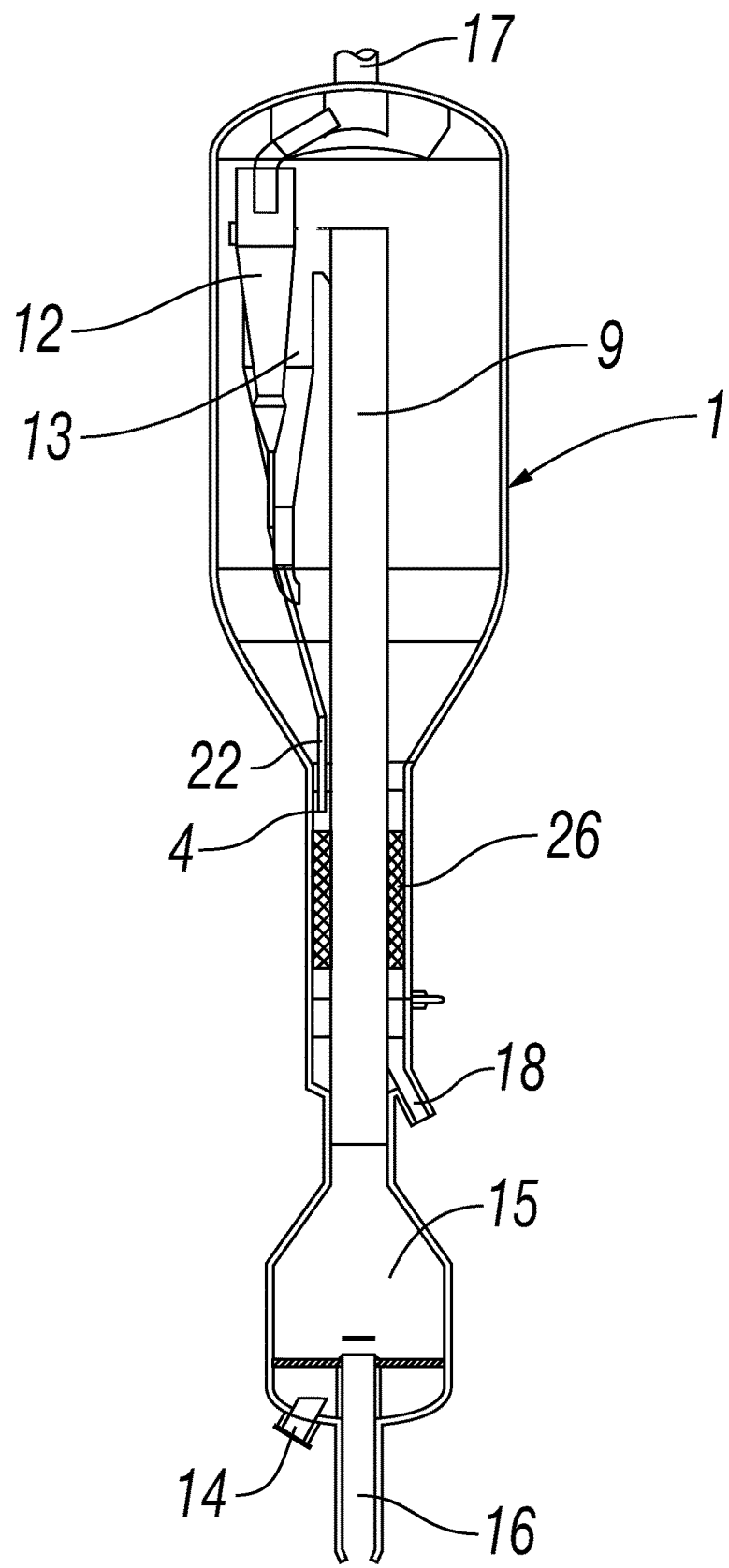
FIG. 1 is a cross-sectional elevational view of an alkane or alkyl aromatic catalytic dehydrogenation reactor and fluidized catalyst stripping unit according to one embodiment of the invention.

Referring to FIG. 1, the inventive fluidized catalyst stripping unit for displacing entrained gas from catalyst particles according to embodiments disclosed herein comprises a vessel 1 having a two-stage cyclonic separation section which includes a primary cyclone 13 and a secondary cyclone 12. Vessel 1 further includes an inlet 9 to feed a particulate-fluid suspension to the two stage cyclonic separation section. Each of the primary and secondary cyclones, 13 and 12, respectively, have an internal cylindrical surface (not shown) which acts to separate a major fraction of the catalyst particulates from the suspension and to form a vortex of reduced particulate content. The secondary cyclone 12 has a secondary cyclone dipleg 22 which ends in a particulate discharge outlet 4. The particulate discharge outlet 4 of the secondary cyclone 12 is submerged in a catalyst bed 24 (shown as small dot shading in FIG. 2). Vessel 1 further includes a product outlet 17, a reactant inlet 14, catalyst inlet 16, reactor section 15, and used catalyst outlet 18. Below the particulate discharge outlet 4 and catalyst bed 24 are stripping section internals 26, shown as cross-hatching in FIG. 1.

In an alternative embodiment, vessel 1 includes more than one set of primary and secondary cyclones. In a particular embodiment, the product entering the product inlet is propane and the catalyst used is a propane dehydrogenation catalyst, as are known in the art.

In another alternative embodiment, vessel 1 includes a single primary cyclonic separation device and one or more secondary cyclones. Primary cyclonic separation devices are known in the art and include, for example, primary cyclones, and systems commercially available under the names VSS, $LD^2$, and $RS^2$. Primary cyclones are described, for example, in U.S. Pat. Nos. 4,579,716; 5,190,650; and 5,275,641.

Figure 2:
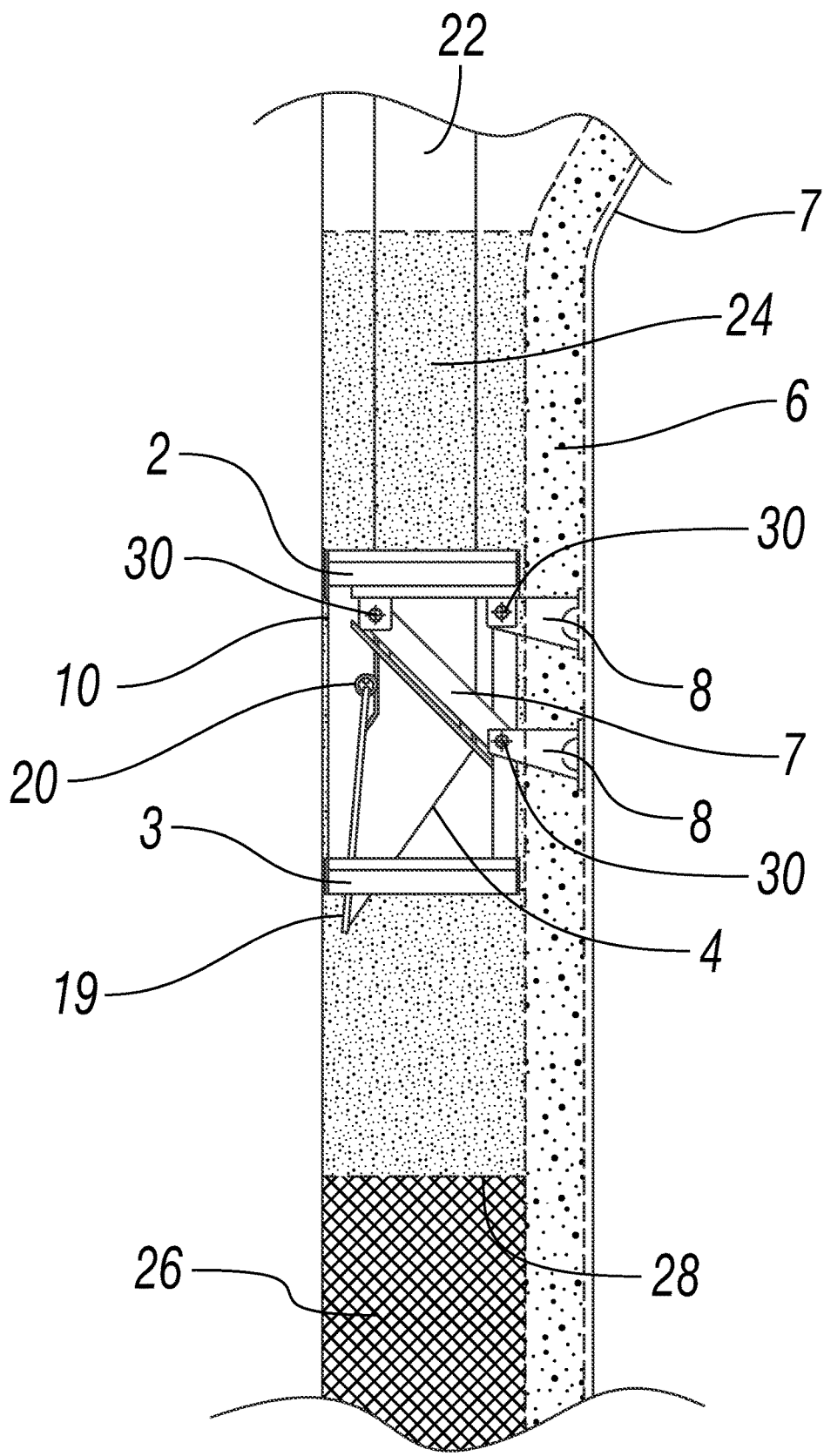
FIG. 2 is a partial cross-sectional elevational view of the stripping section including a secondary cyclone dipleg according to one embodiment of the invention.

As seen in FIG. 2, the catalyst bed 24 extends from the top of stripping section internals (shown as dashed line 28 in FIG. 2) to above a bubble breaking grid 2 located above the particulate discharge outlet 4. Discharge outlet 4 is covered by a hinged cover, shown in FIG. 2 as including a cover 19 secured by a hinged connector 20. Hinged connector 20 may be any mechanism which allows the cover 19 to move away from outlet 4 when pressure is applied from the inside of dipleg 22 and to move against an outer edge of outlet 4 when any such pressure is absent. Such hinged connection ensures one way flow from particulate discharge outlet 4 into catalyst bed 24. Catalyst bed 24 is also present between grids 2 and 3 but is not shown in FIG. 2 so that the details of outlet 4, cover 19 and grids 2 and 3 may be better shown. One or more bubble breaking grid assemblies 2 are located above a bottom portion of the particulate discharge outlet 4. Optionally, one of more bubble breaking grid assemblies 3 are located at or under the level of particulate discharge outlet 4. The grids 2 and 3 may have, in certain embodiments, the forms disclosed in U.S. patent application Ser. No. 14/755,008, filed Jun. 30, 2015 and U.S. patent application Ser. No. 14/751,424, filed Jun. 26, 2015, the disclosures of which are incorporated herein by reference. In the embodiment shown in FIG. 2, grids 2 and 3 are held in place by supports 8. As shown in FIG. 2, grid 3 is suspended from grid 2 by use of hangers 10. Knee brace 7 functions to provide support to grid 2. Knee brace 7 and supports 8 are connected to each other and to grids 2 and 3 by way of hinged connectors 30. In an alternative embodiment, the grids 2 and 3 may be supported by any acceptable method, such as by a cantilevered support, by supports extending across a chord of the vessel, or by a ledge surrounding an interior surface of the vessel.

Figure 3:
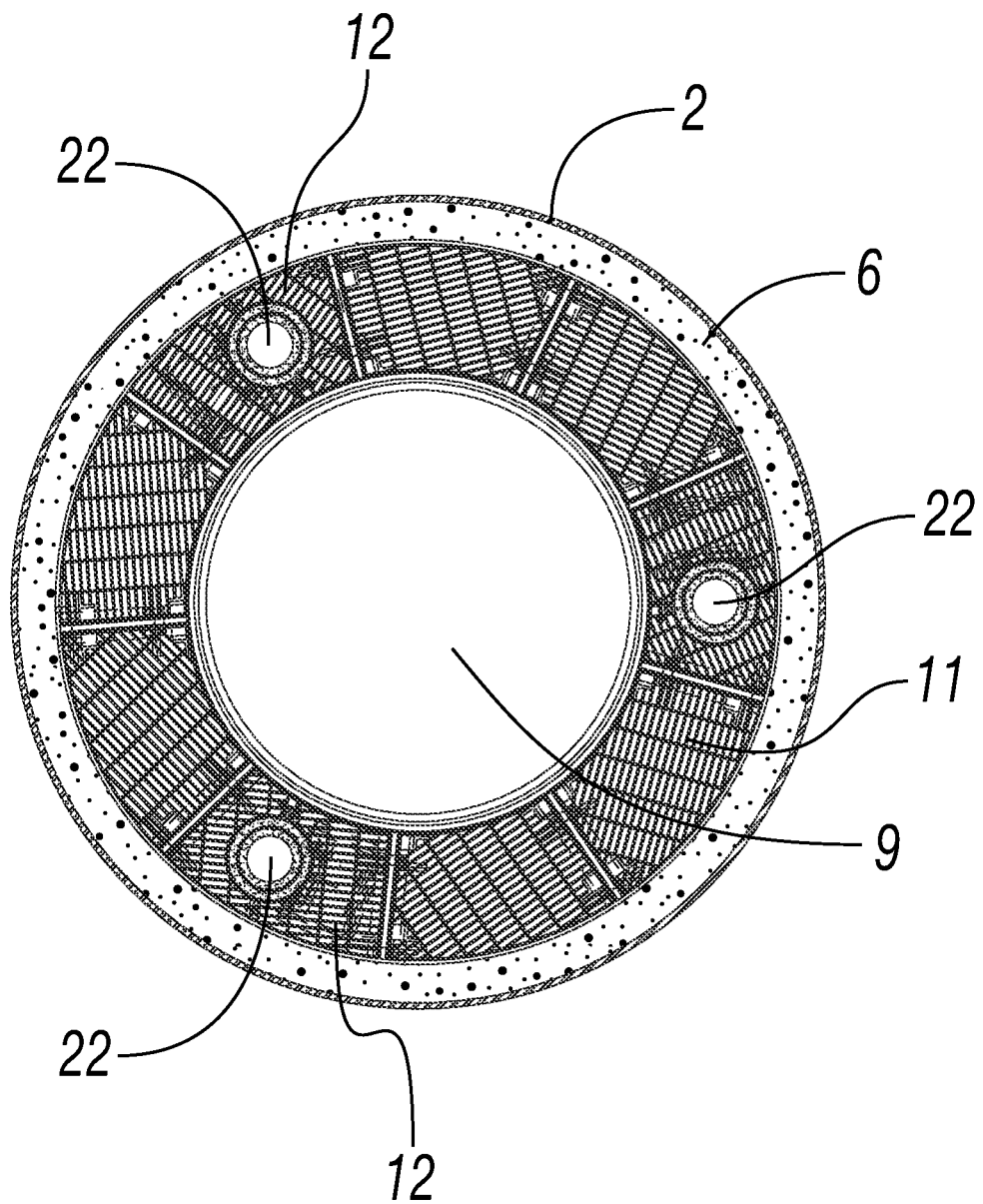
FIG. 3 is a top view of a first bubble breaking grid located at a level above a particulate discharge outlet of the secondary cyclone dipleg.
Figure 4:
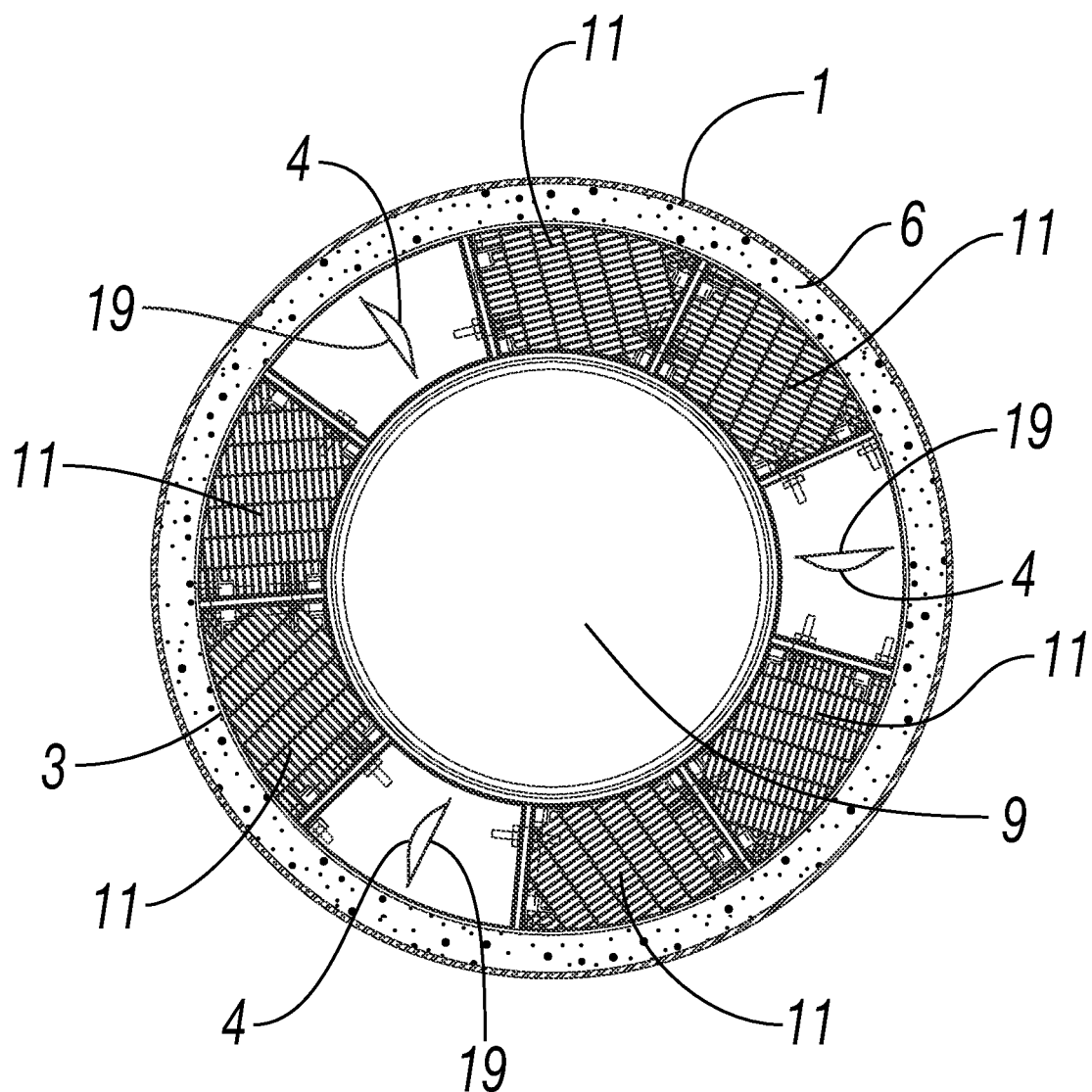
FIG. 4 is a top view of a second bubble breaking grid located at a level of the particulate discharge outlet of the secondary cyclone dipleg.

The large dotted section indicates the presence of an optional refractory material 6 partially or wholly lining the inside of vessel 1. Any appropriate refractory material and anchoring may be used, including for example, RESCO-CAST AA22S, RESCOCAST 4L1, 7, 8, and 9 and R-MAX MP (all of which are commercially available from Resco Products, Inc. (Pittsburgh, Pa., USA), ACTCHEM 85 (commercially available from ARTech Inc.). FIG. 3 illustrates a schematic top view of a first bubble breaking grid 2. Bubble breaking grid 2 is located above the particulate discharge outlet 4. As shown in FIG. 3, grid 2 may be made of a plurality grid section 11. Particular grid sections 12 include open areas to allow dipleg 22 to pass through the grid 2. While FIG. 1 illustrates the presence of a single set of primary and secondary cyclones, FIGS. 3 and 4 illustrate an embodiment in which there are three sets of primary and secondary cyclones. Thus, FIG. 3 shows three diplegs 22, one each from the three secondary cyclones.

FIG. 4 illustrates a schematic top view illustrating bubble breaking grid 3 and particulate discharge outlets 4. As can be seen in FIG. 4, grid sections 11 form bubble breaking grid 3 in a manner similar to bubble breaking grid 2. However, bubble breaking grid 3 may include no grid sections 11 in those areas occupied by particulate discharge outlets 4. As FIG. 4 illustrates an embodiments with three sets of primary and secondary cyclones, FIG. 4 illustrates three particulate discharge outlets 4. As shown in FIG. 4, the particulate discharge outlet 4 faces into the open area between the wall of the vessel 1 and the inlet 9. In FIG. 2, the particulate discharge outlet 4 is shown facing the inlet wall 9. In a preferred embodiment, the outlet 4 is configured as shown in FIG. 4.

In an alternative embodiment, the vessel includes from 1 to 12 twelve cyclone sets. All individual values and subranges from 1 to 12 cyclone sets are included and disclosed herein; for example, the number of dual cyclone sets can range from a lower limit of 1, 3, 5, 7, 9, or 11 to an upper limit of 2, 4, 6, 8, 10, or 12. For example, the vessel may house from 1 to 12 sets of dual cyclones, or in the alternative, from 6 to 12 sets of dual cyclones, or in the alternative, from 1 to 6 sets of dual cyclones, or in the alternative, from 3 to 9 sets of dual cyclones.

In an alternative embodiment, the vessel includes a single primary cyclonic separation device and 1 to 12 secondary cyclones. Primary cyclonic separation devices are known in the art and include, for example, primary cyclones, and systems commercially available under the names VSS, $LD^2$, and $RS^2$.

In an alternative embodiment, the pressure in the vessel 1 may range from 5 to 40 psia. All individual values and subranges from 5 to 40 psia are included and disclosed herein; for example, the pressure can range from a lower limit of 5, 10, 15, 25, or 35 psia to an upper limit of 10, 20, 30 or 40 psia. For example, the pressure in vessel 1 can range from 5 to 40 psia, or in the alternative, from 15 to 25 psia, or in the alternative, from 25 to 40 psia, or in the alternative, from 18 to 38 psia.

In an alternative embodiment, the superficial velocity of gas through the stripper can range from 0.1 to 2 ft/s (feet per second). All individual values and subranges from 0.1 to 2 ft/s are included and disclosed herein; for example, the superficial velocity of the gas can range from a lower limit of 0.1, 0.5, 1, or 1.5 ft/s to an upper limit of 0.3, 0.8, 1.4, 1.8 or 2 ft/s. For example, the superficial velocity can range from 0.1 to 2 ft/s, or in the alternative, from 0.1 to 1 ft/s, or in the alternative from 1 to 2 ft/s, or in the alternative, from 0.5 to 1.5 ft/s.

In an alternative embodiment, the flux of the catalyst through the annular stripper ranges from 1 to 50 $lb/ft^2$ s (pound per $foot^2$+second). All individual values and subranges from 1 to 50 $lb/ft^2$ s are included and disclosed herein; for example, the catalyst flux can range from a lower limit of 1, 10, 20, 30, or 40 $lb/ft^2$ s to an upper limit of 5, 15, 25, 35, 45 or 50 $lb/ft^2$ s. for example, the catalyst flux may range from 1 to 40 $lb/ft^2$ s, or in the alternative, from 1 to 20 $lb/ft^2$ s, or in the alternative, from 20 to 40 $lb/ft^2$ s, or in the alternative, from 10 to 30 $lb/ft^2$ s. Each of the first and second bubble breaking grids have sufficient open areas to permit an actual gas velocity through the grids of less than 8 ft/s. All individual values and subranges from less than 8 ft/s are included and disclosed herein. For example, the actual velocity of gas through the first and second bubble breaking grids can be less than 8 ft/s, or in the alternative, less than 7.0 ft/s, or in the alternative less than 6 ft/s, or in the alternative less than 5 ft/s.

It is known in the art that the static catalyst bed height needed to prevent streaming or bypassing is a function of the freeboard pressure as is shown for example, in the paper entitled "What is Happening Above Your Fluidized Bed? Tools to Maximize FCC Unit Reliability and Turnaround Cycles" presented at the 2010 annual meeting of NPRA. For example, for a freeboard pressure of about 40 kPAg, the static catalyst bed height must be two meters or less in order to prevent streaming or bypassing.

The present invention may be embodied in other forms without departing from the spirit and the essential attributes thereof, and, accordingly, reference should be made to the appended claims, rather than to the foregoing specification, as indicating the scope of the invention.

I claim:

1. A fluidized catalyst stripping unit for displacing entrained gas from catalyst particles comprising:
    a vessel which houses
        a two stage cyclonic separation section which comprises one or more primary cyclonic separation devices and one or more secondary cyclones;
        a stripping section which comprises internals and one or more bubble breaking grids supported by a hinged support system;
        an inlet in fluid communication with a catalytic reactor to feed a particulate-fluid suspension to the two stage cyclonic separation section; and
        a particulate discharge outlet from each secondary cyclone to the stripping section;
    wherein:
        each primary cyclonic separation device comprises an internal cylindrical surface to separate a major fraction of the particulates from the suspension and form a vortex of reduced particulate content;
        the particulate discharge outlet of the secondary cyclone is submerged in a catalyst bed which is located above the stripper internals within the stripping section; and
        the one or more bubble breaking grids are located within the catalyst bed and above the stripping internals.

2. The fluidized catalyst stripping unit according to claim 1, wherein the one or more bubble breaking grids are selected from the group consisting of subway grating, chevrons, packing, round bars, pipes, flat bars, and angle irons.

3. The fluidized catalyst stripping unit according to claim 1, wherein the one or more bubble breaking grids are supported by a cantilevered support system.

* * * * *